United States Patent
Hulse et al.

(10) Patent No.: US 8,497,401 B2
(45) Date of Patent: Jul. 30, 2013

(54) AZEOTROPE-LIKE COMPOSITIONS OF PENTAFLUOROPROPANE, CHLOROTRIFLUOROPROPENE, AND HYRDROGEN FLUORIDE

(75) Inventors: Ryan Hulse, Getzville, NY (US); Rajiv Ratna Singh, Getzville, NY (US); Hsueh Sung Tung, Getzville, NY (US); Ian Shankland, Randolph, NJ (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 13/290,463

(22) Filed: Nov. 7, 2011

(65) Prior Publication Data

US 2012/0053372 A1    Mar. 1, 2012

Related U.S. Application Data

(62) Division of application No. 12/693,208, filed on Jan. 25, 2010, now Pat. No. 8,075,797.

(60) Provisional application No. 61/148,246, filed on Jan. 29, 2009.

(51) Int. Cl.
  *C07C 17/20* (2006.01)
  *C07C 21/20* (2006.01)
  *C09K 5/00* (2006.01)
  *C09K 5/04* (2006.01)
  *C11D 17/00* (2006.01)
  *C11D 17/08* (2006.01)

(52) U.S. Cl.
USPC ........ 570/160; 570/177; 252/67; 252/182.12; 510/408; 510/410; 510/415

(58) Field of Classification Search
USPC   252/182.12, 67; 510/408, 410, 415; 570/160, 570/177
See application file for complete search history.

(56) References Cited

U.S. PATENT DOCUMENTS

| | | | |
|---|---|---|---|
| 5,710,352 | A | 1/1998 | Tung |
| 5,895,825 | A | 4/1999 | Elsheikh et al. |
| 6,013,846 | A | 1/2000 | Wismer et al. |
| 6,060,629 | A | 5/2000 | Pham et al. |
| 6,111,150 | A | 8/2000 | Sakyu et al. |
| 6,328,907 | B1 | 12/2001 | Nakada et al. |
| 6,362,383 | B1 | 3/2002 | Wilmet et al. |
| 6,403,847 | B1 | 6/2002 | Nakada et al. |
| 6,844,475 | B1 | 1/2005 | Tung et al. |
| 7,183,448 | B2 | 2/2007 | Nakada et al. |
| 2008/0098755 | A1 | 5/2008 | Singh et al. |
| 2008/0207788 | A1 | 8/2008 | Bowman et al. |

OTHER PUBLICATIONS

Kim, et al., "A Study To Determine The Existence Of An Azeotropic R-22 "Drop-In" Substitute," prepared by U.S. Department of Commerce for Electric Power Research Institute, Mar. 1996, pp. 1-45, U.S.

Morrison, et al., "Azeotropy In Refrigerant Mixtures," International Journal of Refrigeration, 1993, pp. 129-138, vol. 16, No. 2. U.S.

*Primary Examiner* — Harold Pyon
*Assistant Examiner* — Tanisha Diggs
(74) *Attorney, Agent, or Firm* — Bruce O. Bradford

(57) ABSTRACT

The invention is directed to a ternary azeotrope-like mixture consisting essentially of effective amounts of 1,1,1,3,3-pentafluoropropane, 1-chloro-3,3,3-trifluoropropene, and hydrogen fluoride.

13 Claims, 1 Drawing Sheet

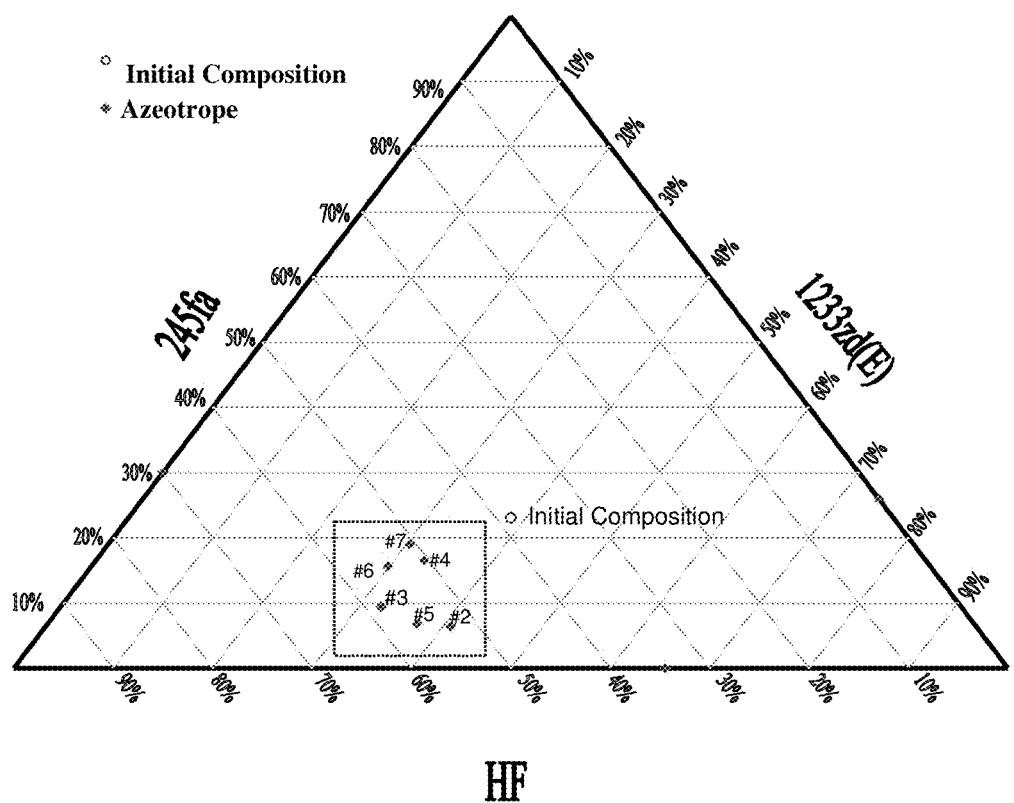

AZEOTROPE-LIKE COMPOSITIONS OF PENTAFLUOROPROPANE, CHLOROTRIFLUOROPROPENE, AND HYRDROGEN FLUORIDE

CROSS-REFERENCE TO RELATED APPLICATIONS

This application is a Divisional of U.S. application Ser. No. 12/693,208, filed on Jan. 25, 2010, now U.S. Pat. No. 8,075,797, which claims priority benefit of U.S. Provisional Application Ser. No. 61/148,246, filed on Jan. 29, 2009, each of which are incorporated herein by reference.

BACKGROUND

1. Field of Invention

The present invention relates to azeotrope-like compositions. More particularly, the invention relates to ternary azeotrope-like compositions comprising hydrohalocarbons and hydrogen fluoride.

2. Description of Prior Art

Fluorocarbon based fluids have found widespread use in industry in a number of applications, including as refrigerants, aerosol propellants, blowing agents, heat transfer media, gaseous dielectrics, fire suppression with or without extinguishing and fire/explosion prevention. However, certain compounds, such as chlorofluoroalkanes and hydrochlorofluoroalkanes are suspected of depleting atmospheric ozone and, thus, are harmful to the environment. Moreover, some of these compounds are believed to contribute to global warming. Accordingly, it is desirable to use halocarbon fluids having low or even zero ozone depletion potential and low global warming potential, such as the entgegen isomer of 1-chloro-3,3,3-trifluoropropene (i.e., E-1-chloro-3,3,3-trifluoropropene or "1233zd(E)").

1233zd(E) has been found to have a wide variety of uses, for example as a heat transfer agent, as a foaming agent, and as a solvent, among other uses, see, e.g., U.S. Patent Publication Nos. 2008/0098755 and 2008/0207788, and U.S. Pat. No. 6,362,383. 1233zd may be produced by a number of different methods. For example, Patent Application Ser. No. 61/047,613, U.S. Pat. Nos. 5,710,352, 6,111,150, and 6,844,475 describe several methods for making 1233zd. Each of the abovementioned publications are herein incorporated by reference in their entirety.

The use of single component fluids or azeotropic mixtures, which do not fractionate on boiling and evaporation, is also desirable. Of particular interest are mixtures containing hydrofluorocarbons, chlorofluoroolefins, and hydrogen fluoride (HF) which are useful in the preparation and/or purification of desirable hydrofluorocarbons and chlorofluoroolefins products. Unfortunately, the identification of new, environmentally-safe, non-fractionating mixtures is complicated due to the fact that azeotrope formation is not readily predictable.

Binary azeotropes between 1233zd and HF, between 1,1,1,3,3-pentafluoropropane (245fa) and HF and between 245fa and 1233zd(E) are known and have been described in U.S. Pat. Nos. 6,013,846, 6,328,907 and 7,183,448, respectively, each of which are incorporated herein by reference. However, there remains a need for ternary azeotropes containing hydrofluorocarbons, chlorofluoroolefins, and HF. Such mixtures are the subject of this invention.

SUMMARY OF THE INVENTION

A ternary azeotrope between 1233zd(E), 245fa and HF has been discovered. This azeotrope is useful in the purification of 1233zd(E), particularly in a separation process associated with the vapor and gas phase process for making 1233zd(E).

Accordingly, a preferred aspect of the invention provides a composition comprising a ternary azeotrope-like mixture consisting essentially of effective amounts of 1,1,1,3,3-pentafluoropropane, 1-chloro-3,3,3-trifluoropropene, and hydrogen fluoride, preferably a ternary azeotrope-like mixture consisting essentially of 25-45 wt % 245fa, 42-65 wt % 1233zd(E), and 0.5-22 wt % HF.

According to another aspect of the invention, provided is a method for producing 1-chloro-3,3,3-trifluoropropene comprising: (a) reacting a starting material comprising at least one hydrochlorocarbon and/or hydrochlorofluorocarbon with a fluorinating agent to produce a reaction product comprising 1-chloro-3,3,3-trifluoropropene, hydrogen fluoride, and 1,1,1,3,3-pentafluoropropane; (b) distilling said reaction product to produce a distillate comprising a ternary azeotrope-like composition according to claim 7; (c) contacting said distillate with sulfuric acid or a caustic solution and subsequently removing at least a portion of said hydrogen fluoride from said distillate to produce a purified distillate comprising said 1-chloro-3,3,3-trifluoropropene and 1,1,1,3,3-pentafluoropropane; and (d) contacting said purified distillate with an extraction media having a selective affinity for 1-chloro-3,3,3-trifluoropropene relative to 1,1,1,3,3-pentafluoropropane and subsequently separating said 1-chloro-3,3,3-trifluoropropene from said 1,1,1,3,3-pentafluoropropane.

BRIEF DESCRIPTION OF THE DRAWINGS

FIG. 1 is a three-component compositional diagram showing azeotrope-like mixtures according to a preferred embodiment of the invention.

DETAILED DESCRIPTION OF PREFERRED EMBODIMENTS OF THE INVENTION

In certain preferred embodiments, the invention is directed to a composition comprising a ternary azeotrope-like mixture consisting essentially of effective amounts of 1233zd(E), 245fa, and HF. Preferably, the ternary azeotrope-like mixture consists of effective amounts of 1233zd(E), 245fa, and HF. Even more preferably, the ternary azeotrope-like mixture consists of about 24 to about 45 wt. % 245fa, about 42 to about 65 wt. % 1233zd(E), and about 0.5 to about 22 wt. % HF, based upon the total weight of the azeotrope-like composition.

As used herein, the term "azeotrope-like" relates to compositions that are strictly azeotropic or that generally behave like azeotropic mixtures. An azeotropic mixture is a system of two or more components in which the liquid composition and vapor composition are equal at the stated pressure and temperature. In practice, this means that the components of an azeotropic mixture are constant-boiling or essentially constant-boiling and generally cannot be thermodynamically separated during a phase change. The vapor composition formed by boiling or evaporation of an azeotropic mixture is identical, or substantially identical, to the original liquid composition. Thus, the concentration of components in the liquid and vapor phases of azeotrope-like compositions change only minimally, if at all, as the composition boils or otherwise evaporates. In contrast, boiling or evaporating non-azeotropic mixtures changes the component concentrations in the liquid phase to a significant degree.

Thus, a characteristic of azeotrope-like compositions is that there is a range of compositions containing the same components in varying proportions that are azeotrope-like or constant boiling. All such compositions are intended to be covered by the terms "azeotrope-like" and "constant boiling". As an example, it is well known that at differing pressures, the composition of a given azeotrope will vary at least slightly, as will the boiling point of the composition. Thus, an azeotrope of A, B, and C represents a unique type of relationship, but with a variable composition depending on temperature and/or pressure. It follows that, for azeotrope-like compositions, there is a range of compositions containing the same components in varying proportions that are azeotrope-like. All such compositions are intended to be covered by the term azeotrope-like as used herein.

As used herein, the term "consisting essentially of", with respect to the components of an azeotrope-like composition, means the composition contains the indicated components in an azeotrope-like ratio, and may contain additional components provided that the additional components do not form new azeotrope-like systems. For example, azeotrope-like mixtures consisting essentially of three compounds are those that form ternary azeotropes, which optionally may include one or more additional components, provided that the additional components do not render the mixture non-azeotropic and do not form an azeotrope with any or all of the specified compounds.

The term "effective amounts" as used herein refers to the amount of each component which, upon combination with the other components, results in the formation of an azeotrope-like composition of the present invention.

In certain preferred embodiments of the composition, the 1,1,1,3,3-pentafluoropropane is present in an amount of about 32.3 to about 40.8 weight percent based upon the total weight of the azeotrope-like composition; the chloro-3,3,3-trifluoropropene is present in an amount of about 52.8 to about 58.3 weight percent based upon the total weight of the azeotrope-like composition; and the hydrogen fluoride is present in an amount of about 6.4 to about 9.4 weight percent based upon the total weight of the azeotrope-like composition, provided that the azeotrope-like composition has a temperature of about 23±1° C. and a pressure of about 23±1 psia.

In certain preferred embodiments of the composition, the 1,1,1,3,3-pentafluoropropane is present in an amount of about 33.0 to about 37.1 weight percent based upon the total weight of the azeotrope-like composition; the 1-chloro-3,3,3-trifluoropropene is present in an amount of about 50.4 to about 56.0 weight percent based upon the total weight of the azeotrope-like composition; and the hydrogen fluoride is present in an amount of about 6.9 to about 16.6 weight percent based upon the total weight of the azeotrope-like composition, provided that the azeotrope-like composition has a temperature of about 70±1° C. and a pressure of about 120±1 psia.

In certain preferred embodiments of the composition, the 1,1,1,3,3-pentafluoropropane is present in an amount of about 29.8 to about 30.3 weight percent based upon the total weight of the azeotrope-like composition; the 1-chloro-3,3,3-trifluoropropene is present in an amount of about 50.6 to about 54.6 weight percent based upon the total weight of the azeotrope-like composition; and the hydrogen fluoride is present in an amount of about 15.6 to about 19.1 weight percent based upon the total weight of the azeotrope-like composition, provided that the azeotrope-like composition has a temperature of about 42±1° C. and a pressure of about 46±1 psia.

The azeotrope-like compositions of the present invention may further include a variety of optional process components including, but not limited to, catalysts, reaction by-products, process starting materials, and the like. Preferably, these optional process components do not affect the basic azeotrope-like characteristics of the composition.

Also provided are methods of producing the azeotrope-like composition comprising reacting HF with a halogenated propane, preferably a pentahalogenated propane, more preferably a pentachloropropane, and most preferably 1,1,1,3,3-pentachloropropane (HCC-240fa) under conditions effective to produce 1233zd(E), 245fa, HF, and optionally, co-products and unreacted starting materials. Another method of producing the azeotrope-like composition involves blending 1233zd (E), 245fa, and HF in amounts effective to produce an azeotrope-like composition. Each of these components can be purchased commercially and/or can be produced by methods known in the art, such as those described herein. Any of a wide variety of methods known in the art for combining three or more components to form a composition can be adapted for use in the present methods to produce an azeotrope-like composition. For example, 1233zd(E), 245fa, and HF can be mixed, blended, or otherwise contacted manually and/or by machine, as part of a batch or continuous reaction and/or process, or via combinations of two or more such steps. In view of the disclosure herein, those of skill in the art will be readily able to prepare azeotrope-like compositions according to the present invention without undue experimentation.

In another preferred embodiment, provided is a method for producing 1-chloro-3,3,3-trifluoropropene comprising: (a) reacting a starting material comprising at least one hydrochlorocarbon and/or hydrochlorofluorocarbons, preferably a pentahalogenated propane, more preferably a pentachloropropane, and most preferably 1,1,1,3,3-pentachloropropane (HCC-240fa) with a fluorinating agent, preferably HF, to produce a reaction product comprising 1-chloro-3,3,3-trifluoropropene, hydrogen fluoride, and 1,1,1,3,3-pentafluoropropane; (b) distilling said reaction product to produce a distillate comprising a ternary azeotrope-like composition according to claim 7; (c) contacting said distillate with sulfuric acid or a caustic solution and subsequently removing at least a portion of said hydrogen fluoride from said distillate to produce a purified distillate comprising said 1-chloro-3,3,3-trifluoropropene and 1,1,1,3,3-pentafluoropropane; and (d) contacting said purified distillate with an extraction media having a selective affinity for 1-chloro-3,3,3-trifluoropropene relative to 1,1,1,3,3-pentafluoropropane and subsequently separating said 1-chloro-3,3,3-trifluoropropene from said 1,1,1,3,3-pentafluoropropane. For example, the production of 1233zd (as described in U.S. Pat. No. 5,710,352, which is incorporated herein by reference) involves reacting 1,1,1,3,3-pentachloropropane (HCC-240fa) with hydrofluoric acid (HF). The product of this reaction contains 1233zd(E), 1,1,1,3,3-pentafluoropropane (245fa), HF and may also contain various impurities. The ternary azeotrope-like mixture can be used to separate and remove the excess HF and other impurities through distillation. The excess HF is then recycled back to the initial reactor. The distillate, which contains the ternary azeotrope-like mixture, can then be further purified using sulfuric acid scrubbing or a caustic solution to remove the HF from the mixture. The resulting solution is a mixture of 1233zd(E) and HFC-245fa. The 1233zd(E) can then be extracted and purified by means of a mineral oil, silicone oil or other extraction media which has a high solubility towards 1233zd(E).

EXAMPLE

The invention is further illustrated in the following example which is intended to be illustrative, but not limiting in any manner.

A sample of 38.5 wt % HFC-HFC-245fa, 38.5 wt % 1233zd(E) and 23 wt % HF was charged into a monel distillation column. The distillation column consisted of a 1 L reboiler connected to a 1" diameter by 4' long column. The column was packed with Helipak high efficiency monel packing. The condenser was cooled using a thermostated propylene glycol water solution.

The distillation column was operated at full reflux and allowed to reach temperature and pressure equilibrium at each of the desired conditions. Once the column had achieved equilibrium a vapor sample was taken from the overhead of the distillation column. The column was again operated at full reflux for an additional 15 minutes and a second vapor sample was taken from the distillation column. The concentrations of HFC-245fa, 1233zd(E) and HF in each sample were then analyzed by standard methods. The distillation column was operated at 23° C., 70° C. and 42° C. in that order and two samples were collected and analyzed at each condition. The temperature and pressure were measured to within ±2° C. and ±2 psi, respectively. FIG. 1 and Table 1 show the initial composition of the material charged into the reboiler along with the measured azeotropic compositions. The azeotrope like composition ranged from 25 wt %-45 wt % 254fa, 42 wt %-65 wt % 1233zd(E), and 0.5 wt %-22 wt % HF as outline by a dashed line (------) in FIG. 1.

TABLE 1

Azeotrope like compositions of 245fa, 1233zd(E) and HF.

| | Temp, ° C. ± 2° C. | Press, psia ± 2 psi | Sample Composition | | |
|---|---|---|---|---|---|
| | | | HF | HFC-245fa | 1233zd(E) |
| Sample 2 | 23 | 23 | 6.4% | 40.8% | 52.8% |
| Sample 3 | 23 | 23 | 9.4% | 32.3% | 58.3% |
| Sample 4 | 70 | 120 | 16.6% | 33.0% | 50.4% |
| Sample 5 | 70 | 120 | 6.9% | 37.1% | 56.0% |
| Sample 6 | 42 | 46 | 15.6% | 29.8% | 54.6% |
| Sample 7 | 42 | 46 | 19.1% | 30.3% | 50.6% |

Having thus described a few particular embodiments of the invention, various alterations, modifications, and improvements will readily occur to those skilled in the art. Such alterations, modifications, and improvements, as are made obvious by this disclosure, are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A method for producing 1-chloro-3,3,3-trifluoropropene comprising:
   a. reacting a starting material comprising at least one hydrochlorocarbon and/or hydrochlorofluorocarbon with a fluorinating agent to produce a reaction product comprising 1-chloro-3,3,3-trifluoropropene, hydrogen fluoride, and 1,1,1,3,3-pentafluoropropane;
   b. distilling said reaction product to produce a distillate comprising a ternary azeotrope-like composition comprising an effective amount of 1,1,1,3,3-pentafluoropropane, 1-chloro-3,3,3-trifluoropropene, and hydrogen fluoride; and
   c. contacting said distillate with one or more substances to separate at least a portion of said 1-chloro-3,3,3-trifluoropropene, hydrogen fluoride, and/or 1,1,1,3,3-pentafluoropropane from said distillate, wherein said 1-chloro-3,3,3-trifluoropropene, hydrogen fluoride, and/or 1,1,1,3,3-pentafluoropropane are separated in an amount sufficient to break said ternary azeotrope-like composition.

2. The method of claim 1 wherein said contacting involves contacting said distillate with sulfuric acid or a caustic solution and subsequently removing at least a portion of said hydrogen fluoride from said distillate to produce a purified distillate comprising said 1-chloro-3,3,3-trifluoropropene and 1,1,1,3,3-pentafluoropropane.

3. The method of claim 2 further comprising contacting said purified distillate with an extraction media having a selective affinity for 1-chloro-3,3,3-trifluoropropene relative to 1,1,1,3,3-pentafluoropropane and subsequently separating said 1-chloro-3,3,3-trifluoropropene from said 1,1,1,3,3-pentafluoropropane.

4. The method of claim 1 wherein said starting material comprises 1,1,1,3,3-pentachloropropane.

5. The method of claim 1 wherein said ternary azeotrope-like composition comprises 1,1,1,3,3-pentafluoropropane in an amount of about 24 to about 45 weight percent based upon the total weight of the azeotrope-like mixture; 1-chloro-3,3,3-trifluoropropene in an amount of about 42 to about 65 weight percent based upon the total weight of the azeotrope-like mixture; and hydrogen fluoride in an amount of about 0.5 to about 22 weight percent based upon the total weight of the azeotrope-like mixture.

6. The method of claim 1 wherein said ternary azeotrope-like composition comprises 1,1,1,3,3-pentafluoropropane in an amount of about 32.3 to about 40.8 weight percent based upon the total weight of the azeotrope-like mixture; 1-chloro-3,3,3-trifluoropropene in an amount of about 52.8 to about 58.3 weight percent based upon the total weight of the azeotrope-like mixture; and hydrogen fluoride in an amount of about 6.4 to about 9.4 weight percent based upon the total weight of the azeotrope-like mixture, provided that said azeotrope-like mixture has a temperature of about 23±2° C. and a pressure of about 23±2 psia.

7. The method of claim 1 wherein said ternary azeotrope-like composition comprises 1,1,1,3,3-pentafluoropropane in an amount of about 33.0 to about 37.1 weight percent based upon the total weight of the azeotrope-like mixture; 1-chloro-3,3,3-trifluoropropene in an amount of about 50.4 to about 56.0 weight percent based upon the total weight of the azeotrope-like mixture; and hydrogen fluoride in an amount of about 6.9 to about 16.6 weight percent based upon the total weight of the azeotrope-like mixture, provided that said azeotrope-like mixture has a temperature of about 70±2° C. and a pressure of about 120±2 psia.

8. The method of claim 1 wherein said ternary azeotrope-like composition comprises 1,1,1,3,3-pentafluoropropane in an amount of about 29.8 to about 30.3 weight percent based upon the total weight of the azeotrope-like mixture; 1-chloro-3,3,3-trifluoropropene is present in an amount of about 50.6 to about 54.6 weight percent based upon the total weight of the azeotrope-like mixture; and hydrogen fluoride in an amount of about 15.6 to about 19.1 weight percent based upon the total weight of the azeotrope-like mixture, provided that said azeotrope-like mixture has a temperature of about 42±2° C. and a pressure of about 46±2 psia.

9. A method for producing 1-chloro-3,3,3-trifluoropropene comprising:
   a. reacting a starting material comprising at least one hydrochlorocarbon and/or hydrochlorofluorocarbon with a fluorinating agent to produce a reaction product comprising 1-chloro-3,3,3-trifluoropropene, hydrogen fluoride, and 1,1,1,3,3-pentafluoropropane;

b. distilling said reaction product to produce a distillate comprising a ternary azeotrope-like composition comprising an effective amount of 1,1,1,3,3-pentafluoropropane, 1-chloro-3,3,3-trifluoropropene, and hydrogen fluoride;
c. contacting said distillate with sulfuric acid or a caustic solution to remove at least a portion of said hydrogen fluoride and produce a second distillate comprising 1,1,1,3,3-pentafluoropropane, 1-chloro-3,3,3-trifluoropropene; and
d. contacting said second distillate with an extraction media having a selective affinity for one of 1-chloro-3,3,3-trifluoropropene or 1,1,1,3,3-pentafluoropropane and separating 1-chloro-3,3,3-trifluoropropene from 1,1,1,3,3-pentafluoropropane.

10. The method of claim 9, wherein the distillate is contacted with sulfuric acid.

11. The method of claim 9, wherein the extraction media has selective affinity to 1-chloro-3,3,3-trifluoropropene.

12. The method of claim 11, wherein the extraction media comprises mineral oil.

13. The method of claim 11, wherein the extraction media comprises silicone oil.

* * * * *